United States Patent
Murali

(10) Patent No.: US 11,471,891 B2
(45) Date of Patent: *Oct. 18, 2022

(54) BENCHTOP INCUBATOR

(71) Applicant: SciTech Consultants, LLC, Orangeburg, SC (US)

(72) Inventor: Anuradha Murali, Orangeburg, SC (US)

(73) Assignee: SciTech Consultants, LLC, Orangeburg, SC (US)

( * ) Notice: Subject to any disclaimer, the term of this patent is extended or adjusted under 35 U.S.C. 154(b) by 305 days.

This patent is subject to a terminal disclaimer.

(21) Appl. No.: 15/174,168

(22) Filed: Jun. 6, 2016

(65) Prior Publication Data
US 2017/0348693 A1    Dec. 7, 2017

(51) Int. Cl.
*B01L 9/00* (2006.01)
*G01N 1/44* (2006.01)
*B01L 1/02* (2006.01)

(52) U.S. Cl.
CPC .............. *B01L 9/523* (2013.01); *B01L 1/025* (2013.01); *G01N 1/44* (2013.01); *B01L 2200/02* (2013.01); *B01L 2300/06* (2013.01); *B01L 2300/0822* (2013.01); *B01L 2300/0829* (2013.01); *B01L 2300/18* (2013.01)

(58) Field of Classification Search
CPC ...... B01L 1/025; B01L 9/523; B01L 2200/02; B01L 2300/06; B01L 2300/18; B01L 2300/0822; B01L 2300/0829; G01N 1/44
USPC ............................................ 435/303.1, 289.1
See application file for complete search history.

(56) References Cited

U.S. PATENT DOCUMENTS

| | | | |
|---|---|---|---|
| 1,598,585 A | | 8/1926 | Almendinger |
| 2,364,722 A | * | 12/1944 | Kazantzeff ............. A01K 41/00 119/318 |
| 2,505,360 A | * | 4/1950 | Jeffreys ................... C12N 9/242 435/203 |
| 3,712,268 A | * | 1/1973 | Reed ..................... A01K 41/023 119/319 |
| 3,746,161 A | * | 7/1973 | Jones ......................... B01L 9/52 206/456 |
| 4,689,303 A | * | 8/1987 | Kraft ......................... B01L 7/00 126/21 A |

(Continued)

FOREIGN PATENT DOCUMENTS

| | | |
|---|---|---|
| EP | 2484750 | 8/2012 |
| EP | 3255137 | 12/2017 |

(Continued)

OTHER PUBLICATIONS

Emura, Takayuki, "English language machine translation of JP-2006149232-A". (Year: 2006).*

(Continued)

*Primary Examiner* — Liban M Hassan
(74) *Attorney, Agent, or Firm* — Dority & Manning, P.A.

(57) ABSTRACT

A bench top incubator is described. The bench top incubator includes a first tray stack designed to retain microscope slides in a plurality of slide trays and a second tray stack designed to retain multi-well plates in a plurality of plate trays. The incubator is relatively simple and small in design and can be conveniently located to carry out temperature processing of biological samples such as fixed cells and tissues, biological fluids, and so forth.

19 Claims, 4 Drawing Sheets

(56) References Cited

U.S. PATENT DOCUMENTS

| | | | |
|---|---|---|---|
| 5,266,272 | A | 11/1993 | Griner et al. |
| 5,525,512 | A | 6/1996 | Pieler et al. |
| 5,577,821 | A | 11/1996 | Chu |
| 5,985,653 | A | 11/1999 | Armstrong et al. |
| 6,238,031 | B1 | 5/2001 | Weng |
| 6,238,032 | B1 | 5/2001 | Cooper et al. |
| 6,258,325 | B1 | 7/2001 | Sanadi |
| 6,271,022 | B1 * | 8/2001 | Bochner .............. G01N 35/028 356/388 |
| 6,367,900 | B1 | 4/2002 | Woerner |
| 6,465,242 | B1 * | 10/2002 | Kanipayor ............. C12M 23/08 219/386 |
| 7,029,080 | B2 | 4/2006 | Barry, Jr. et al. |
| 7,112,241 | B2 | 9/2006 | Sha |
| 8,511,765 | B1 | 8/2013 | Chen et al. |
| 2003/0031602 | A1 | 2/2003 | Weselak et al. |
| 2006/0093514 | A1 * | 5/2006 | Dawes ..................... B01L 7/00 422/44 |
| 2007/0217964 | A1 * | 9/2007 | Johnson ................ C12M 35/04 422/130 |
| 2010/0112577 | A1 | 5/2010 | Chu |
| 2010/0291664 | A1 * | 11/2010 | Herbert ..................... B01L 1/02 435/286.2 |
| 2010/0315628 | A1 * | 12/2010 | Mertsching ........ G01N 15/1463 356/301 |
| 2011/0183411 | A1 | 7/2011 | Nichols et al. |
| 2011/0315783 | A1 * | 12/2011 | Baker ....................... B01L 7/52 236/3 |
| 2013/0050692 | A1 * | 2/2013 | Tang .................... B01L 3/50855 356/246 |
| 2015/0299639 | A1 | 10/2015 | Kleefstra et al. |
| 2017/0073628 | A1 | 3/2017 | Zander et al. |
| 2019/0211300 | A1 | 7/2019 | Murali |

FOREIGN PATENT DOCUMENTS

| | | | | | |
|---|---|---|---|---|---|
| GB | | 2481041 | A * | 12/2011 | ............ C12M 23/22 |
| JP | | 2006149232 | A * | 6/2006 | ............ C12M 23/04 |
| KR | 10-2011-0122291 | | | 11/2011 | |
| KR | | 101137507 | B1 * | 4/2012 | ............ C12M 21/16 |
| WO | WO 2007/120619 | | | 10/2007 | |
| WO | WO 2017/214087 | | | 12/2017 | |

OTHER PUBLICATIONS

Jung et al., "English machine translation of KR 10-1137507 B1". (Year: 2011).*
PCT International Search Report dated Aug. 24, 2017 (3 pages).
BIOGENE Multi Room Incubator (XP-002790814) and Dual Chamber Incubator (XP-002790601) *Biotechnologies, Inc.* www.biotechnologies.com.

* cited by examiner

BENCHTOP INCUBATOR

BACKGROUND

The incubation of fixed cells and other non-living biological samples at designated conditions is common in a large variety of molecular and biological techniques such as immunohistochemistry, immunocytochemistry, enzyme-linked immunosorbent assay (ELISA), in situ reverse transcription polymerase chain reaction (RT-PCR), and so forth. Such incubation is in many ways simpler than incubation of live cells. For instance, incubation of fixed cells does not require sterile incubation conditions or highly specific gaseous atmospheric control (e.g., $CO_2$ control).

Unfortunately, the relatively simpler processes of such incubations leads to incubation protocols that have lower reproducibility and therefore less confidence. For instance, when incubating at room temperature, fixed cell systems (e.g., plates or slides) are simply held at whatever "room temperature" may be in that particular laboratory, which can vary widely from one laboratory to another. Issues also exist for lower and higher temperature non-live cell incubation systems. Lower temperature incubation is generally carried out by simply placing the samples in a laboratory refrigerator that is very rarely (if ever) calibrated and very rarely includes a temperature log. Higher temperature incubations are either carried out by use of a warm room that is similarly neither calibrated nor logged or by use of existing high performance incubation systems that have been developed for use with live cell cultures. These high performance systems provide reproducible conditions, but are much more complex and expensive than necessary when considering incubation of non-live cell systems such as fixed tissues, serum, etc.

What is needed in the art is an incubator that can provide well calibrated but less complicated incubation capabilities for biological samples. An incubator that can improve reproducibility of laboratory protocols and that is less expensive, smaller, and more user-friendly than high performance incubation systems necessary for live cell incubation would be of great benefit in the art.

SUMMARY

According to one embodiment, disclosed is a bench top incubator configured for use with biological systems (e.g., fixed cells or tissues, serum, biological fluids, etc.). The benchtop incubator can include a first tray stack and a second tray stack that are adjacent to one another. The first tray stack is configured to retain a plurality of vertically stacked slide trays, with each slide tray comprising one or more slide insets. Each slide inset can be sized to retain an individual microscope slide. In one embodiment, each slide inset can also include access insets that can improve handling capabilities when placing or retrieving microscope slides on a slide tray. The second tray stack is configured to retain a plurality of vertically stacked plate trays, each of which including an inset configured to retain a multi-well plate, e.g., a 96-well plate.

A bench top incubator can also include a temperature control system and optionally also a timing control system that can control the temperature of a chamber of the incubator and as such can control the temperature of the samples retained within the incubator housing. In one embodiment, the tray stacks can be thermally isolated from one another, allowing for independent temperature control of the different tray stacks and of different samples.

Also disclosed are methods for utilizing the incubators. For example, a method can include locating a biological sample on a microscope slide or in a multi-well plate, retaining the slide or plate on a tray, and placing the tray in an incubator. The incubator chamber holding the sample can then be held at a predetermined temperature for a desired time period.

BRIEF DESCRIPTION OF THE DRAWINGS

A full and enabling disclosure of the present disclosure, including the best mode thereof, to one of ordinary skill in the art, is set forth more particularly in the remainder of the specification, including reference to the accompanying drawings in which.

Figure 1:
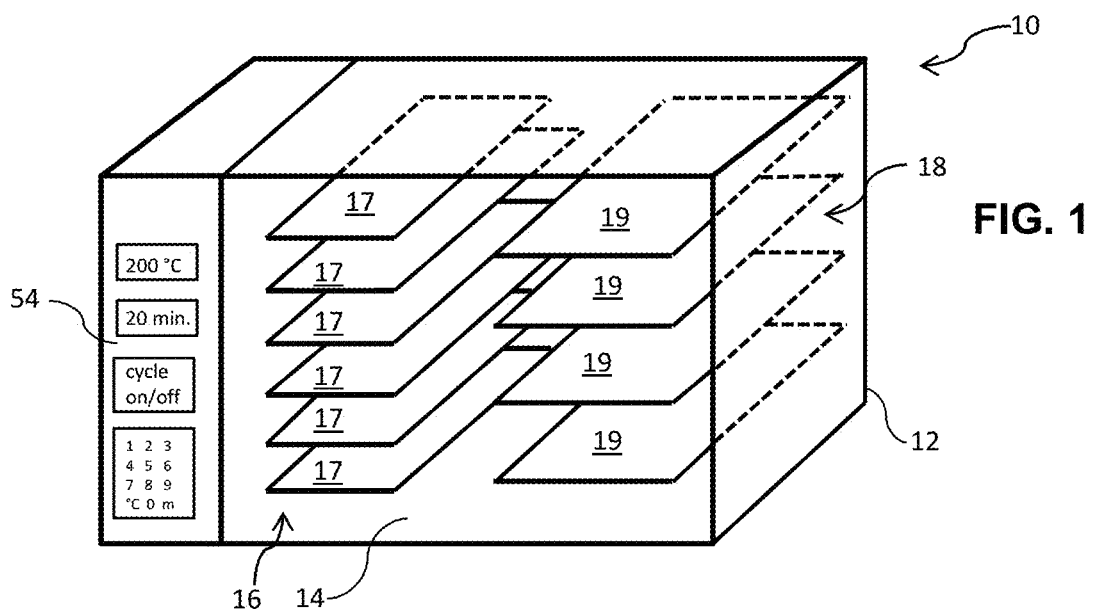
FIG. 1 schematically illustrates one embodiment of a bench top incubator as described herein.

Repeat use of reference characters in the present specification and drawings is intended to represent the same or analogous features or elements of the present invention.

DETAILED DESCRIPTION

Reference now will be made in detail to embodiments of the disclosure, one or more examples of which are set forth below. Each example is provided by way of explanation, not limitation of the disclosed subject matter. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

The present disclosure is generally directed to a bench top incubator that can be utilized in a wide variety of research activities. More specifically, the bench top incubators disclosed herein can accommodate both microscope slides and multi-well plates in a relatively small and inexpensive incubation system.

Referring to FIG. 1, one embodiment of a bench top incubator 10 is illustrated. The incubator 10 includes a housing 12 that defines an interior chamber 14 that can be thermally isolated from the surrounding environment.

The chamber 14 is configured to retain therein a first tray stack 16 and a second tray stack 18. The first tray stack 16 can include a plurality of slide trays 17, each of which being configured to retain one or more microscope slides, and the second tray stack 18 can include a plurality of plate trays 19, each of which being configured to retain one or more multi-well plates. As illustrated, the slide trays 17 and the plate trays 19 are not of the same dimensions as one another, but this is not a requirement of the bench top incubator.

While the incubator 10 illustrated in FIG. 1 includes only a first and second tray stack 16, 18, it should be understood that a bench top incubator as disclosed herein is not intended to be limited to any particular number of tray stacks or any particular number of trays within each tray stack. However, the bench top incubator is generally understood to be relatively small, so as to be portable and stable when located on a typical bench top. For instance, the housing 12 can generally be about 1.5 cubic meter (1.5 m$^3$) or less in outer volume. In one embodiment, each outer dimension of the housing can be about 1.5 meter or less.

Housing 12 can include an access door (not shown on FIG. 1), which can generally be disposed in a forwardly facing panel of the housing 12, but could as well be located in other panels of the housing 12, provided it allows access to the tray stacks within.

The housing includes 12 defines a chamber 14 that is a thermally controlled chamber for, e.g., culturing of fixed tissues or cells, biological fluids, serum etc. By way of example, the thermally controlled chamber 14 and include inner and outer spaced apart walls. The outer walls, inner walls and door can be formed of any suitable material such as, for example stainless steel, but may be manufactured from other suitable materials such as aluminum, ceramics, and/or high temperature plastic (e.g., acrylonitrile butadiene styrene (ABS)) as a matter of design choice. The walls surrounding the thermally controlled chamber 14 can include an insulation material within the surrounding walls as is generally known in the art such as expanded urethane.

The chamber 14 can be sized to hold two or more tray stacks 16, 18. By way of example, a chamber 14 can define an internal volume of about 1 m$^3$ or less, about 0.75 m$^3$ or less, or about 0.5 m$^3$ or less in some embodiments. The small volume of the incubator chamber 14 can ensure improved temperature uniformity by positioning the plate trays 16, 18 at a consistent spacing from the inner walls.

Figure 2:
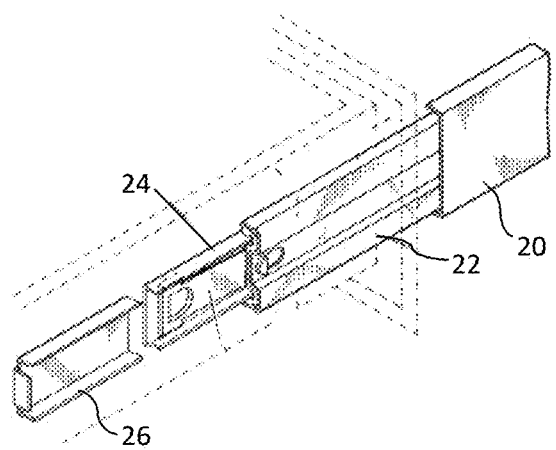
FIG. 2 illustrates one embodiment of a mounting bracket as may be utilized in conjunction with an individual tray of an incubator.

Each of the plate trays 17, 19 can be contained within the incubator chamber 14 in an accessible fashion by use of a suitable bracket or holding device as is generally known in the art. By way of example, and without limitation, FIG. 2 illustrates one typical sliding bracket that includes an outer rail 20, an intermediate rail 22, an inner rail 24, and a stop section 26. As shown, the various sections of the sliding bracket nest within one another and are slidingly engaged with one another. In use, a sliding bracket can be attached to either side of an individual tray 17, 19 (an example of which is shown in dashed lines in FIG. 2). When a single tray is drawn out to an accessible position, a pulling force can slide the sections 20, 22, 24, 26, out from one another as shown. A single tray can thus be pulled out, e.g., out of a door at the front of the chamber 14, for access. Similarly, by pushing against the stop section 26, the rails can telescope in and the tray can be returned to a storage space within the chamber.

Any suitable bracket system is incorporated herein, including immobile brackets that simply support the trays held thereon. Exemplary bracket systems include, without limitation, those described in U.S. Pat. No. 6,238,032 to Cooper, et al.; U.S. Pat. No. 6,367,900 to Woerner; U.S. Pat. No. 7,029,080 to Barry, Jr., et al.; U.S. Pat. No. 8,511,765 to Chen, et al.; U.S. Pat. No. 5,577,821 to Chu; and U.S. Pat. No. 6,258,325 to Sanadi; all of which are incorporated herein by reference.

Figure 3:
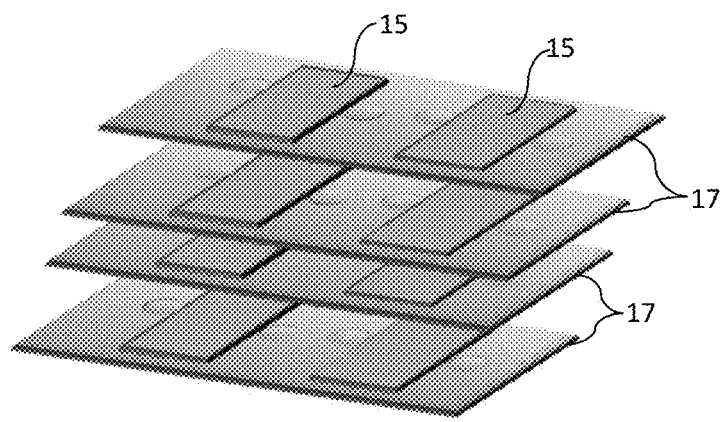
FIG. 3 schematically illustrates one embodiment of a tray stack including a plurality of vertically stacked slide trays.

FIG. 3 illustrates one example of a plurality of slide trays 17 as may form a tray stack 16. In the illustrated embodiment, each slide tray 17 is configured to retain two microscope slides 15, however, this is not a requirement of a bench top incubator, and a slide tray can be configured to retain 1, 2, 3, or more microscope slides.

Figure 4:
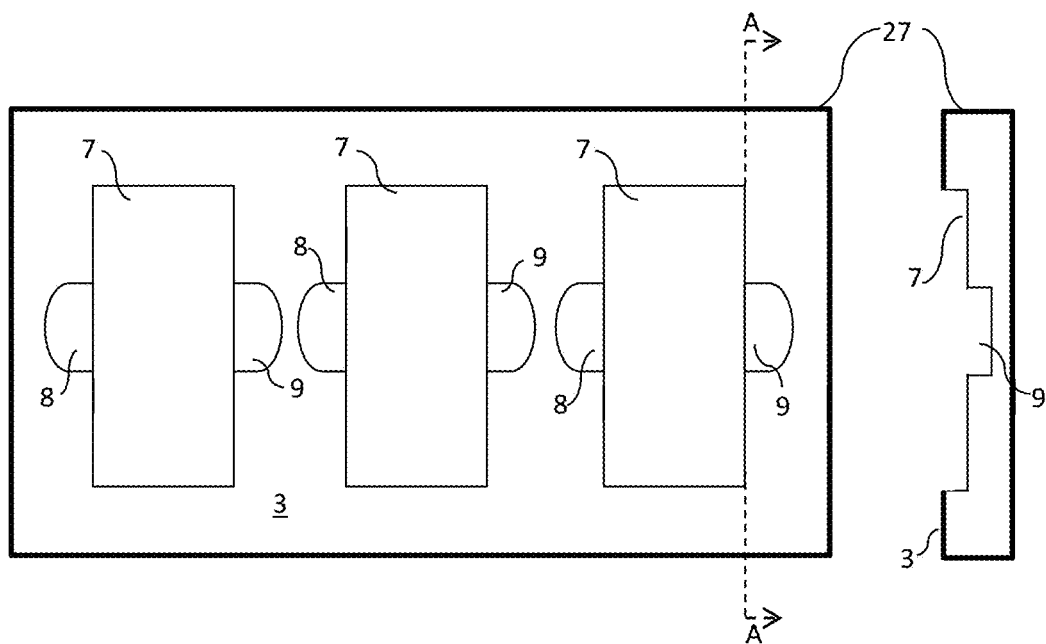
FIG. 4 schematically illustrates a top view and a side view of one embodiment of a slide tray.

A single slide tray 17 is illustrated in FIG. 4 including a top view (left) and a side view (right) taken along the line A-A. A slide tray 17 can be formed of any suitable material capable of withstanding expected conditions within an incubator. For instance, slide tray 17 can be formed of a suitable temperature stable plastic, e.g., ABS, or the like and may be formed according to standard methods such as, without limitation, injection molding. A slide tray 17 can include suitable hardware as necessary to be retained in a chamber 14 by use of the desired bracket system.

In the embodiment of FIG. 4, the slide tray 27 is configured to retain three microscope slides at three slide insets 7. The slide insets 7 can generally be sized so as to retain a typical microscope slide, e.g., about 75 millimeters (mm) by about 26 mm in surface area and generally about 1 mm in height. An individual slide inset 7 can have any suitable depth (as seen in the side view of the slide tray 27) to retain a slide therein. The depth of a slide inset can be for instance about 2 mm or less, for example from about 0.1 mm to about 1.5 mm in some embodiments, or from about 0.5 mm to about 1 mm in some embodiments.

Figure 5:
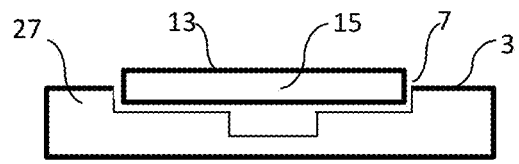
FIG. 5 schematically illustrates a side view of a slide tray and a microscope slide retained thereon.

It should be understood that a slide inset 7 need only be deep enough to retain a microscope slide in the designated area. As such, it can be shallower than a typical microscope slide thickness (generally about 1 mm). As illustrated in a side view of a slide tray 27 in FIG. 5, in such an embodiment, the upper surface 13 of a microscope slide 15 may extend above the upper surface 3 of the slide tray 27 when the microscope slide 15 is retained in the slide inset 7. Of course, a slide inset can be the same depth as the microscope slide, such that the surfaces are coplanar or can be deeper such that the surface of the microscope slide is below the surface of the slide tray.

Figure 6:
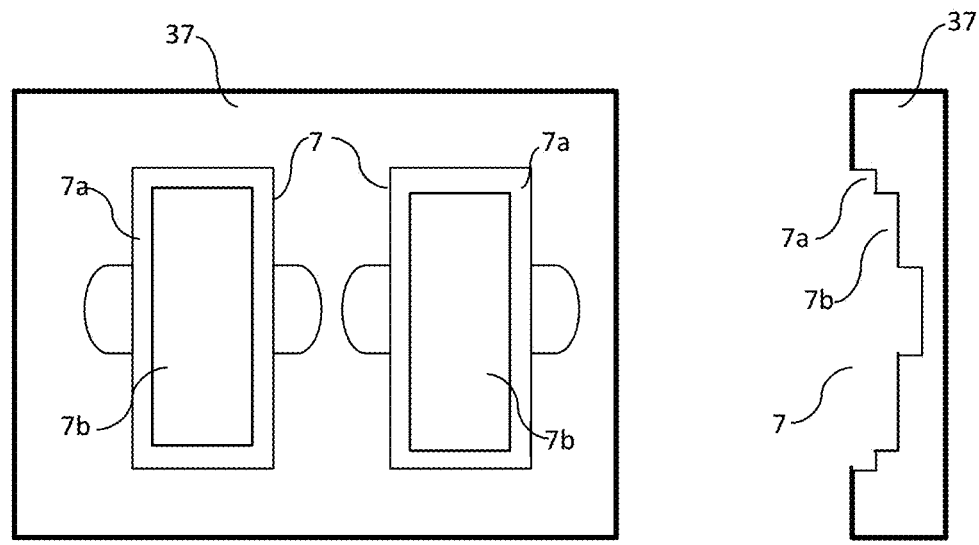
FIG. 6 schematically illustrates a top view and a side view of one embodiment of a slide tray.

In one embodiment a single slide inset can be configured to retain microscope slides of different sizes. FIG. 6 illustrates an example of one such embodiment in a top view (left) and a side view (right). As seen in FIG. 6, a slide tray 37 defines two slide insets 7. Each slide inset 7 further defines a first inset 7a and a second nested inset 7b that is deeper than the first inset 7a. The first inset 7a can thus be sized to retain a microscope slide of a first size, and the second inset 7b can be sized to retain a microscope slide of a second, smaller size.

Figure 7:
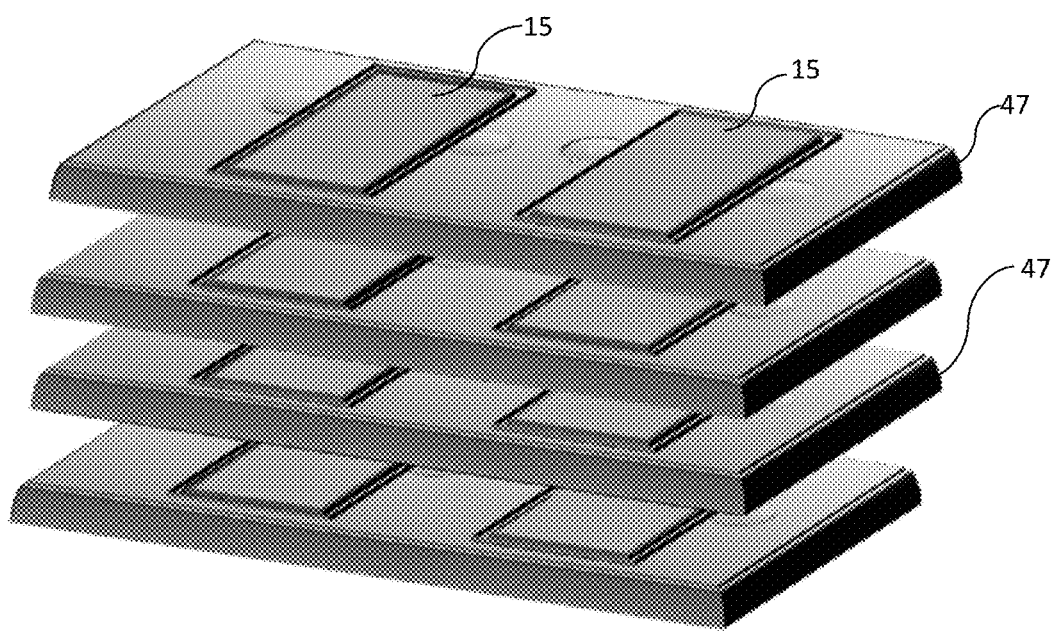
FIG. 7 schematically illustrates another embodiment of a tray stack including a plurality of vertically stacked slide trays.

FIG. 7 illustrates another embodiment of a slide tray 47. As illustrated, the dimensions of the slide tray 47 are somewhat different than the dimensions of the slide tray 17 of FIG. 3 and the slide tray 27 of FIG. 4. The particular dimensions of any slide tray can be varied according to the size of the bench top incubator, the number of tray stacks to be included in the incubator, the number of slides to be retained on each slide tray, the bracket system used to retain the slide tray within the chamber, the materials of construction, etc. as is known in the art.

According to one embodiment, the slide insets of a slide tray can optionally include access insets that can ease placing and removal of slides from a slide tray. For example, and as illustrated in FIG. 3-FIG. 7, the individual slide insets can include access insets on either side of the slide inset. With particular reference to FIG. 4, a slide inset 7 can include a first access inset 8 and a second access inset 9 located on opposite sides from one another of the slide inset 7. The access insets 8, 9 can have any suitable shape and depth so as to allow an individual to grasp a microscope slide retained in the slide inset 7. For example, in the illustrated embodiment, the access insets 8, 9 have a generally semi-circular cross section, but this is not a requirement of the devices, and any suitable shape can be utilized.

As shown in the side view of FIG. 4, the access inset 9 can generally be slightly deeper than the slide inset 7, as this can aid in grasping a slide retained in the slide inset 7. By way of example, an access inset 8, 9, can generally have a depth within a slide tray of about 2 mm or less, for instance from about 1 mm to about 2 mm or about 1.5 mm in some embodiments.

Figure 8:
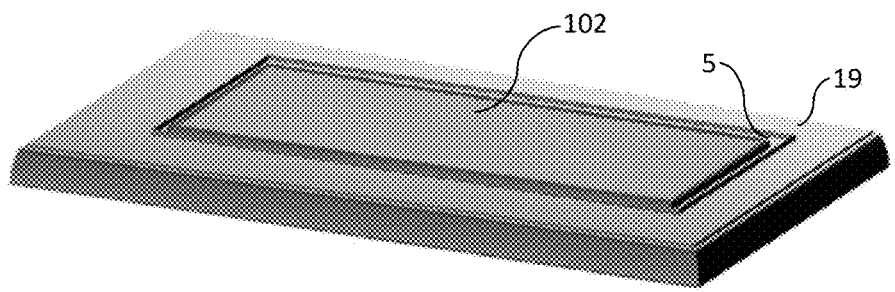
FIG. 8 schematically illustrates one embodiment of a plate tray.

Referring again to FIG. 1, a bench top incubator 10 can include a second tray stack 18 that includes a plurality of plate trays 19. FIG. 8 illustrates one embodiment of a plate tray 19 as may be incorporated in a bench top incubator. As illustrated, a plate tray 19 can include a plate inset 5 configured to retain a multi-well plate 107 therein.

A plate tray can be formed of similar materials as a slide tray, or of different materials, as desired. In some embodiments, a plate tray 19 can have somewhat larger dimensions than a slide tray, but this is not a requirement of a bench top incubator, and is generally due to the fact that the multi-well plates retained in a plate tray tend to be larger than the slides retained in a slide tray. In addition, a plate tray can generally be held in a chamber 14 of an incubator 10 by use of a similar bracket system as is utilized to retain the slide trays therein. This is not a requirement of an incubator, but the system should allow for access to the multi-well plates held within the incubator.

Figure 9:
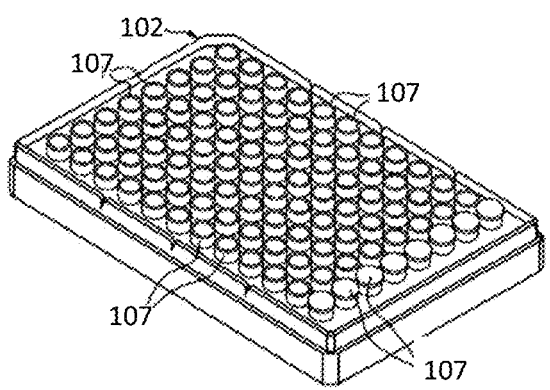
FIG. 9 schematically illustrates a multi-well plate as may be retained on a plate tray.

FIG. 9 illustrates a typical multi-well plate 102 as may be retained by use of a plate tray. In this particular embodiment, the multi-well plate 102 is a 96-well plate that defines 96 individual wells 107 as shown. Each well 107 includes a rim, sidewalls, and a bottom according to standard practice. The wells 107 are generally arranged in a matrix of mutually perpendicular rows and columns. For example, the multi-well plate 102 can include a matrix of wells 107 having dimensions of 4×6 (24 wells), 8×12 (96 wells) or 16×24 (384 wells).

While the plate tray 19 illustrated in FIG. 8 is designed to retain a single multi-well plate 102, the disclosed incubators are not limited to this design, and in other embodiments, a plate tray may be designed to retain multiple plates. The preferred number of multi-well plates to be retained on a single plate tray can generally depend upon the size of the incubator and the size of the multi-well plates to be retained. In addition, a plate tray can include a series of nested plate insets, similar to the nested slide insets described above, so as to be configured to retain multi-well plates of various sizes.

Figure 10:
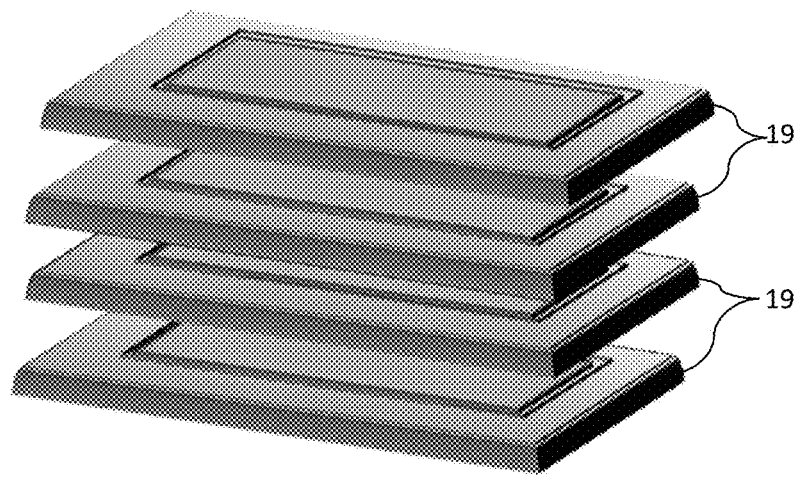
FIG. 10 schematically illustrates one embodiment of a tray stack including a plurality of vertically stacked plate trays.

FIG. 10 demonstrates a tray stack of four multi-well plate trays 19 as may be included in a bench top incubator. Through utilization of a suitable bracket system, for instance as described previously, each plate tray 19 can be individually accessed during use of the bench top incubator.

Though illustrated in FIG. 1 as including a single thermal chamber 14, a bench top incubator is not limited to a single chamber. For instance, in the embodiment illustrated in FIG. 11, a bench top incubator 110 includes a first chamber 114 and a second chamber 115 that are thermally isolated from one another.

In this particular embodiment, the first tray stack 16 including the slide trays 17 are retained within the chamber 115 and the second tray stack 18 including the plate trays 19 are retained within the chamber 114, but the division of the various plate trays between thermally isolated chambers of an incubator can be as desired. For instance, each thermally isolated chamber can include one or more slide trays in conjunction with one or more plate trays.

The chambers 114, 115 can be separated from one another by a thermally insulating wall as is known in the art. For example, a thermally insulating wall 120 can include a first and second wall with an insulative material there between, as described above with regard to the outer housing of an incubator.

A bench top incubator can also include a control assembly that can be used to control the temperature within the chamber(s) of the incubator. In one embodiment, a control system can also control the timing of an incubation within the chamber(s).

By way of example and with reference to FIG. 1, a temperature control assembly 54 can be operatively coupled with the housing 12 to control the temperature within the chamber 14 so that the temperature remains within a desired range. For example, in one application, the control assembly 54 can maintain the temperature within the chamber 14 at a predetermined temperature of from about 2° C. to about 150° C. with high accuracy, for instance such that the chamber temperature is maintained within a range of the predetermined temperature of about ±1.0° C., ±0.5° C., or ±0.2° C.

A temperature control assembly 54 can include components as are generally known in the art including a heater, a controller and a temperature sensor. The proximity of the temperature sensor to the heater, in combination with the constrained volume of the chamber 14, can allow the temperature control assembly 54 to maintain a uniform temperature within the chamber 14.

In general, a heater can be positioned between the outer walls and the inner walls of the housing 12 and is operable for heating the incubation chamber 14 when the internal temperature in the incubator 10 is below the incubators desired operating temperature. The heater may be any conventional heating device. By way of example, a heater can include a low watt density, high surface area, contact resistive heater. The temperature system 54 can include a temperature controller that can direct electrical power from a power supply (not shown) to cycle the heater. The controller may be any conventional programmable microprocessor device. In one embodiment, the temperature control system may be coupled to a timer according to conventional methodology.

A temperature sensor can generally be mounted within the housing 12 for monitoring the temperature within the incubation chamber 14, for instance inside an inner wall of the housing 12 so that it monitors the temperature within the incubation chamber 14. As is known, a temperature sensor can be coupled with a controller for delivering signals representative of the sensed temperature thereto.

Figure 11:
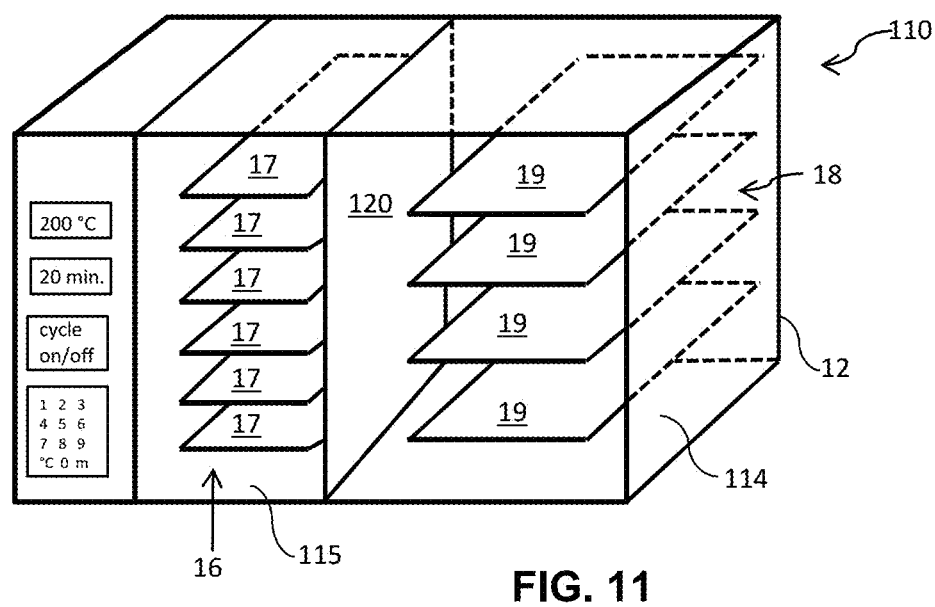
FIG. 11 schematically illustrates one embodiment of a bench top incubator including thermally isolated tray stacks.

In those embodiments in which an incubator includes multiple thermally insulated chambers, for example as illustrated in FIG. 11, the temperature control system can include additional components in communication with one another, as is known in the art.

In operation, an operator can place a slide and/or a multi-well plate carrying a sample onto a tray in the incubator. Any biological sample obtained from any source is encompassed herein, though, as stated previously, the bench top incubator is generally not designed for use in live cell incubations. Beneficially, as the bench top incubator is not intended for incubation of living cells, it can be of a simpler design. For example, the bench top incubator need not include gas flow and isolation systems for, e.g., $CO_2$ control. In addition, the bench top system can be a non-sterile system and as such need not include materials and devices to insure sterility of a sample, as it is generally intended for use in incubation of non-sterile biological samples.

A sample can be pre-processed according to methodology as is known in the art prior to placement on a slide or into a multi-well plate. Beneficially, the bench top incubator can be utilized with a single sample, multiple different samples or a plurality of identical samples. For instance, a biological sample derived from a first source can be located in a multi-well plate and a biological sample derived from a second source can be located in a different multi-well plate or on a slide and both can be placed in the incubator for thermal incubation or controlled standard temperature (e.g., 25° C.) incubation. Similarly, multiple different plates/slides can carry samples obtained from the same source, but the samples can be pre-processed according to different methodologies.

Another of the benefits of the bench top incubator is the capacity of the incubator for a large number of slides and multi-well plates. For instance, should a protocol call for the incubation of a large number of slides, the plate trays or the plate tray brackets can be utilized to carry slide trays, thereby increasing the capacity of the incubator for additional slides. Moreover, and depending upon the relative size of the slide trays and the plate trays, in one embodiment additional plate trays can be retained on unused slide trays or by use of slide tray brackets, thereby increasing the multi-well plate capacity of the incubator.

Following placement of the sample(s) onto the multi-well plate(s) and/or slide(s), an operator can establish the desired temperature of the chamber 14 either prior to or following the insertion of one or more slides and/or multi-well plates on to the respective trays of the incubator. An operator can adjust the controller of the temperature control assembly 54 to the desired temperature by use of an accessible panel of the control assembly 54. A temperature control assembly 54 can be utilized to establish and maintain the temperature within the incubation chamber 14 for a desired amount of time. For instance, whenever the internal temperature in the chamber 14 is lower than the desired operating temperature of the incubator 10, the controller can cycle power to the heater to maintain the operating temperature of the chamber 14 within a desired range.

While certain embodiments of the disclosed subject matter have been described using specific terms, such description is for illustrative purposes only, and it is to be understood that changes and variations may be made without departing from the spirit or scope of the subject matter.

What is claimed is:

1. A bench top incubator comprising:
   a housing comprising a top and a bottom, a vertical direction of the bench top incubator being defined from the top to the bottom of the housing;
   a first chamber within the housing;
   a first tray stack within the first chamber, the first tray stack comprising a first series of brackets spaced apart from one another in the vertical direction;
   a plurality of slide trays, each slide tray having a first width that is perpendicular to the vertical direction, each slide tray being retained by a bracket of the first tray stack such that the plurality of slide trays are retained in a vertically stacked arrangement on the first tray stack, each slide tray including multiple slide insets defined in an upper surface thereof, each slide inset comprising an inset sized to retain and mate with a microscope slide;
   a second tray stack within the housing and horizontally adjacent to the first tray stack, the second tray stack comprising a second series of brackets vertically spaced apart from one another in the vertical direction, the vertical spacing between each of the vertically adjacent brackets of the second series of brackets being greater than the vertical spacing between each of the vertically adjacent brackets of the first series of brackets;
   a plurality of plate trays, each plate tray having a second width that is perpendicular to the vertical direction, the second width of each plate tray being greater than the first width of each slide tray, each plate tray being retained by a bracket of the second tray stack such that the plurality of plate trays are retained in a vertically stacked arrangement on the second tray stack with the number of plate trays being less than the number of slide trays, each plate tray including one or more plate insets defined in an upper surface thereof, each plate inset comprising an inset sized to retain and mate with a multi-well plate.

2. The bench top incubator of claim 1, the first and second tray stacks both being within the first chamber, the first chamber having a volume of about 1.5 m³ or less.

3. The bench top incubator of claim 1, each slide inset including one or more nested insets.

4. The bench top incubator of claim 1, each slide inset further comprising access insets.

5. The bench top incubator of claim 1, wherein the first series of brackets and the second series of brackets comprise sliding brackets.

6. The bench top incubator of claim 1, each plate tray comprising only a single plate inset.

7. The bench top incubator of claim 1, each plate inset comprising one or more nested insets.

8. The bench top incubator of claim 1, each plate inset comprising an inset sized to retain and mate with a 96-well plate.

9. The bench top incubator of claim 1, further comprising a second chamber, the first and second chambers being thermally isolated from one another.

10. The bench top incubator of claim 9, the second tray stack being within the second chamber.

11. The benchtop incubator of claim 1, further comprising a first temperature sensor for sensing the temperature inside the first chamber, a temperature controller coupled to the first temperature sensor, and a heater electrically connected to the temperature controller.

12. The bench top incubator of claim 9, further comprising a first temperature sensor for sensing the temperature in the first chamber and a second temperature sensor for sensing the temperature inside the second chamber.

13. The bench top incubator of claim 1, wherein an upper surface of a lower slide tray is open to a lower surface of an upper slide tray immediately above that lower slide tray and wherein an upper surface of a lower plate tray is open to a lower surface of an upper plate tray immediately above that lower plate tray.

14. The benchtop incubator of claim 1, wherein each slide inset is sized to retain and mate with a microscope slide having dimensions of about 75 millimeters by about 26 millimeters and about 1 millimeter in height.

15. The bench top incubator of claim 11, further comprising a timer.

16. The benchtop incubator of claim 1, further comprising a plurality of microscope slides that removably nest within the slide insets.

17. The benchtop incubator of claim 1, further comprising a plurality of multi-well plates that removably nest within the plate insets.

18. A benchtop incubator comprising:
- a housing comprising a top and a bottom, a vertical direction of the bench top incubator being defined from the top to the bottom of the housing;
- a first chamber within the housing;
- a first tray stack within the first chamber, the first tray stack comprising a first series of brackets spaced apart from one another in the vertical direction;
- a plurality of slide trays, each slide tray having a first width that is perpendicular to the vertical direction, each slide tray being retained by a bracket of the first tray stack such that the plurality of slide trays are retained in a vertically stacked arrangement on the first tray stack, each slide tray including multiple slide insets defined in an upper surface thereof, each slide inset comprising an inset sized to retain and mate with a microscope slide;
- a second tray stack within the housing and horizontally adjacent to the first tray stack, the second tray stack comprising a second series of brackets vertically spaced apart from one another in the vertical direction, the vertical spacing between each of the vertically adjacent brackets of the second series of brackets being greater than the vertical spacing between each of the vertically adjacent brackets of the first series of brackets;
- a plurality of plate trays, each plate tray having a second width that is perpendicular to the vertical direction, the second width of each plate tray being greater than the first width of each slide tray, each plate tray being retained by a bracket of the second tray stack such that the plurality of plate trays are retained in a vertically stacked arrangement on the second tray stack with the number of plate trays being less than the number of slide trays; wherein
- the benchtop incubator is free of any circulation fans.

19. The benchtop incubator of claim 18, further including only a single control assembly, the single control assembly consisting of one or more temperatures sensors for sensing one or more temperatures inside the benchtop incubator, a temperature controller coupled to the one or more temperature sensors, a heater electrically connected to the temperature controller, and optionally a timer for controlling the timing of an incubation within the benchtop incubator.

* * * * *